United States Patent
Swayze et al.

(10) Patent No.: US 11,246,670 B2
(45) Date of Patent: *Feb. 15, 2022

(54) MODULAR SURGICAL ROBOTIC TOOL

(71) Applicant: Ethicon Endo-Surgery, LLC, Guaynabo, PR (US)

(72) Inventors: Jeffrey S. Swayze, Hamilton, OH (US); Frederick E. Shelton, IV, Hillsboro, OH (US); David C. Yates, West Chester, OH (US); Jason L. Harris, Lebanon, OH (US); Kevin L. Houser, Springboro, OH (US)

(73) Assignee: Cilag GmbH International, Zug (CH)

( * ) Notice: Subject to any disclaimer, the term of this patent is extended or adjusted under 35 U.S.C. 154(b) by 1114 days.

This patent is subject to a terminal disclaimer.

(21) Appl. No.: 15/238,007

(22) Filed: Aug. 16, 2016

(65) Prior Publication Data

US 2018/0049795 A1 Feb. 22, 2018

(51) Int. Cl.
| | |
|---|---|
| *A61B 18/12* | (2006.01) |
| *A61B 34/35* | (2016.01) |
| *A61B 34/30* | (2016.01) |
| *A61B 17/32* | (2006.01) |
| *A61B 18/14* | (2006.01) |

(Continued)

(52) U.S. Cl.
CPC ...... *A61B 34/35* (2016.02); *A61B 17/320092* (2013.01); *A61B 18/1445* (2013.01); *A61B 34/30* (2016.02); *A61B 2017/00221* (2013.01); *A61B 2017/00477* (2013.01); *A61B 2017/00725* (2013.01); *A61B 2017/320093* (2017.08); *A61B 2017/320094* (2017.08); *A61B 2018/00172* (2013.01); *A61B 2018/00178* (2013.01); *A61B 2018/00988* (2013.01); *A61B 2018/1226* (2013.01); *A61B 2090/0803* (2016.02)

(58) Field of Classification Search
None
See application file for complete search history.

(56) References Cited

U.S. PATENT DOCUMENTS 8,114,345 B2   2/2012   Dlugos, Jr. et al.
8,672,922 B2 *  3/2014  Loh ................... A61B 1/00149
                                                              606/1

(Continued)

FOREIGN PATENT DOCUMENTS

WO       WO 00/30548 A1    6/2000

OTHER PUBLICATIONS

International Search Report and Written Opinion for PCT/US2017/046453 dated Nov. 14, 2017 (11 pages).

(Continued)

*Primary Examiner* — Linda C Dvorak
*Assistant Examiner* — Ryan T Clark
(74) *Attorney, Agent, or Firm* — Mintz Levin Cohn Ferris Glovsky and Popeop, P.C.

(57) ABSTRACT

A robotic surgical arm can include a puck containing motors to drive an end effector. A tool assembly attached to the puck generates ultrasonic and/or radio frequency energy to apply between the jaws of the end effector. The tool assembly can include modular components such as a modular shaft that can include an ultrasonic transducer, nonvolatile memory, wireless interface, and/or a power source. The power source allows the tool assembly and modular shaft to communicate wirelessly with the robotic arm.

14 Claims, 15 Drawing Sheets

(51) Int. Cl.
    *A61B 90/00*  (2016.01)
    *A61B 18/00*  (2006.01)
    *A61B 17/00*  (2006.01)

(56) References Cited

U.S. PATENT DOCUMENTS

| | | |
|---|---|---|
| 8,882,792 B2 | 11/2014 | Dietz et al. |
| 8,915,842 B2 | 12/2014 | Weisenburgh, II et al. |
| 8,931,682 B2 | 1/2015 | Timm et al. |
| 8,945,098 B2 | 2/2015 | Seibold et al. |
| 2004/0133189 A1* | 7/2004 | Sakurai ........... A61B 34/70 606/1 |
| 2007/0088245 A1* | 4/2007 | Babaev ........... A61H 23/0245 604/22 |
| 2008/0081948 A1 | 4/2008 | Weisenburgh et al. |
| 2009/0171372 A1* | 7/2009 | Mohr ........... A61B 18/24 606/130 |
| 2011/0118709 A1 | 5/2011 | Burbank |
| 2011/0118778 A1 | 5/2011 | Burbank |
| 2013/0041219 A1* | 2/2013 | Hasegawa ........... A61B 34/76 600/109 |
| 2013/0253480 A1 | 9/2013 | Kimball et al. |
| 2013/0282052 A1 | 10/2013 | Aranyi et al. |
| 2014/0005718 A1 | 1/2014 | Shelton, IV et al. |
| 2014/0236894 A1 | 8/2014 | Hoffman |
| 2014/0276951 A1 | 9/2014 | Hourtash |
| 2015/0141981 A1* | 5/2015 | Price ........... A61B 18/1445 606/38 |
| 2015/0257903 A1 | 9/2015 | Perry |
| 2018/0049794 A1 | 2/2018 | Swayze et al. |

OTHER PUBLICATIONS

Correlated Solutions, "Principle of Digital Image Correlation," 2013 (http://correlatedsolutions.com/digital-image-correlation/).
U.S. Appl. No. 15/131,963 entitled "Method for Operating a Surgical Instrument" filed on Apr. 18, 2016.
U.S. Appl. No. 15/177,430 entitled "Surgical Instrument With User Adaptable Techniques" filed on Jun. 9, 2016.

* cited by examiner

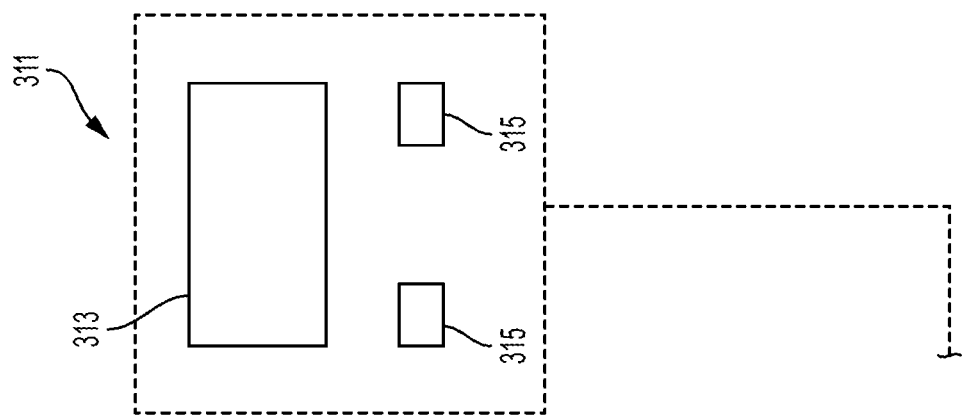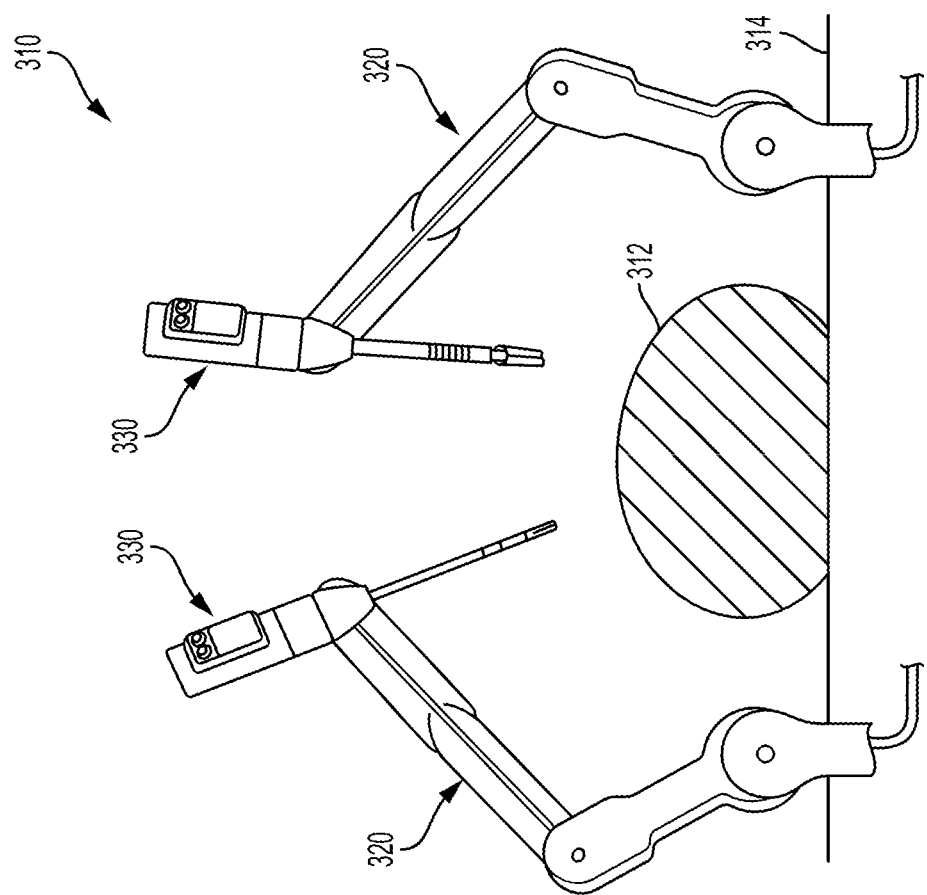
FIG. 1

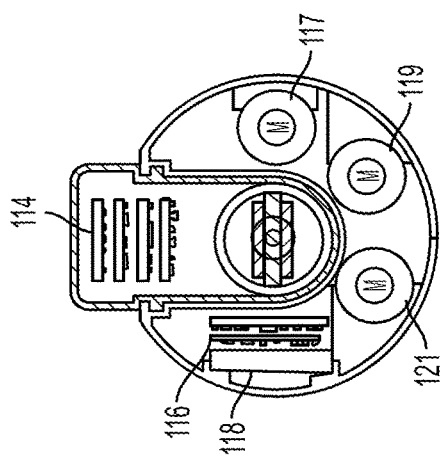
FIG. 8B END VIEW
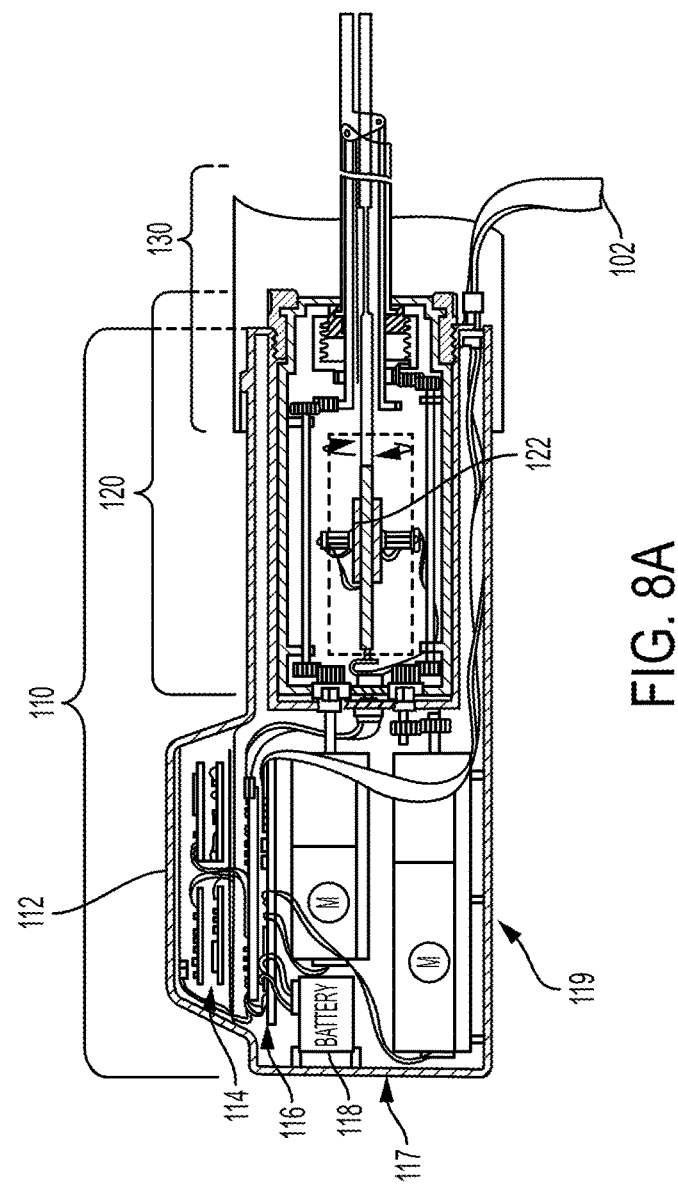
FIG. 8A

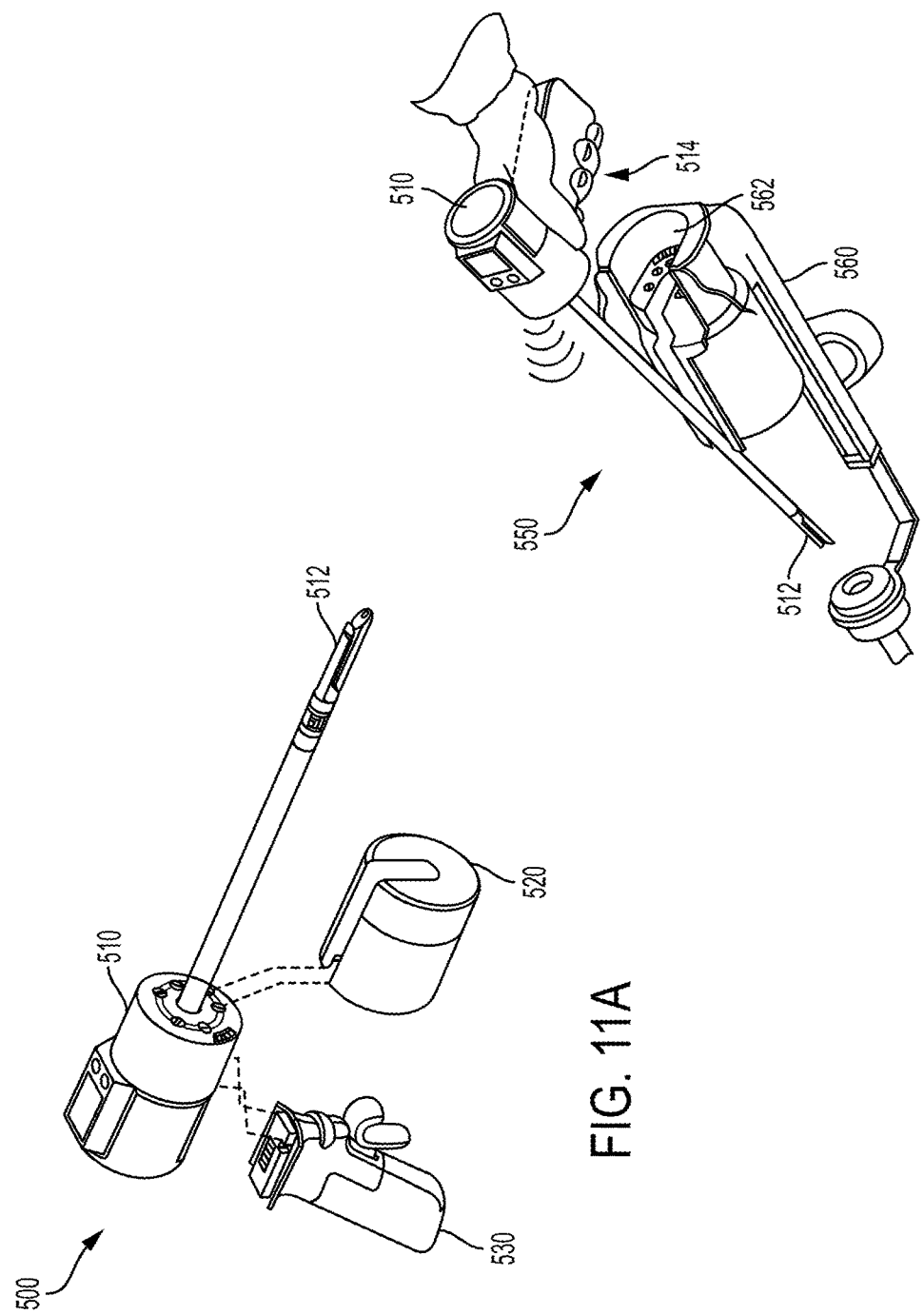

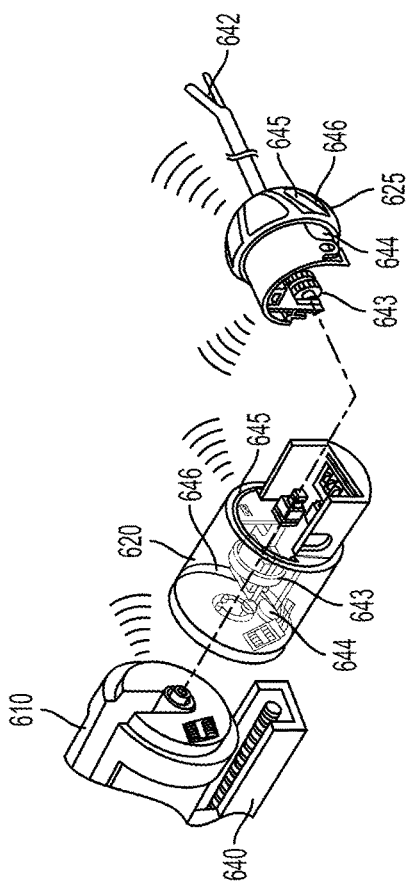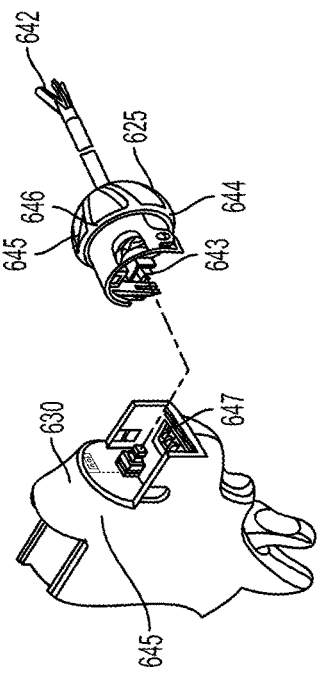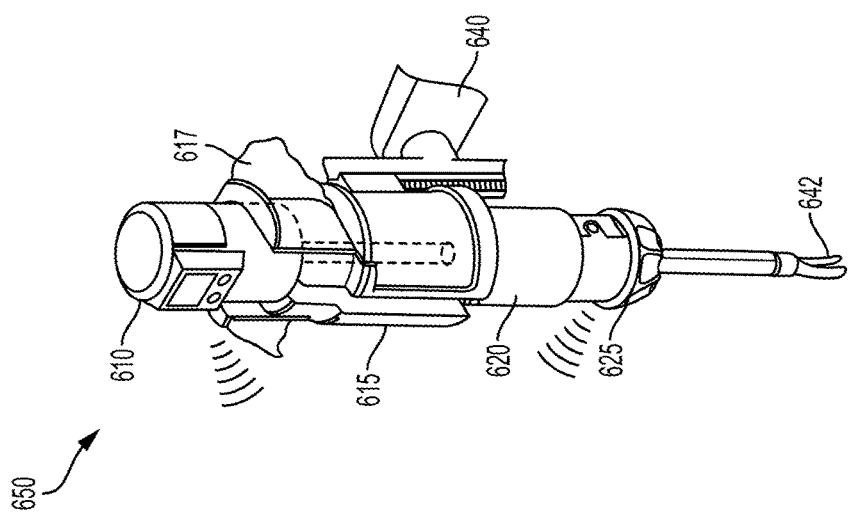
FIG. 12B
FIG. 12C
FIG. 12A

MODULAR SURGICAL ROBOTIC TOOL

FIELD

Methods and devices are provided for robotic surgery, and in particular for wireless communications between components of a robotic surgical system.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems can provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In an embodiment an electromechanical surgical tool includes a tool attachment which has a tool shaft that extends distally therefrom and an end effector at the distal end of the tool shaft. A proximal end of the tool shaft is configured to mechanically and electrically connect to a tool driver, whereby the tool driver supplies electrical power to the tool attachment when connected to the tool attachment. The tool also includes memory to store information about usage of the tool attachment, and an ultrasonic transducer.

The surgical tool can vary in a number of ways. For example, the tool attachment can further include a waveguide and the tool attachment is configured to be a disposable component. In one aspect the tool attachment is removably and replaceably connected to the tool driver. Further, the tool attachment may be configured to be releasably and replaceably connected to a surgeon operated handle.

In another configuration, the tool includes a radio frequency generator, wherein the generator is configured to deliver radio frequency energy to at least one tissue contacting electrode disposed on the end effector.

The surgical tool may utilize a wireless communication channel configured to communicate with the tool driver when the tool attachment is connected to the tool driver, and to communicate with the tool driver when the tool attachment is not connected to the tool driver.

In another embodiment the tool may be configured to utilize a battery to provide power to the tool attachment when the tool driver is disconnected from the tool attachment. Additionally, the memory may be configured to store information related to a calibration of the ultrasonic energy transducer.

In some configurations the tool driver is attached to a robotic arm, which. In such a configuration, the tool attachment may be connected to the tool driver at a first time, removed from the tool driver at a second time, and attached to a surgeon operated handle at a third time, wherein the configuration and calibration information stored in the memory at the first time is read by a processor in the handle at the third time. In some aspects, the third time is later than the second time and the second time is later than the first time.

The surgical tool may be attached to a surgical robotic arm, and the tool attachment may be removably and replaceably attached to a robotic arm, wherein the tool attachment may be released from the robot arm, and attached to another robot arm.

In another aspect, a surgical method involves: connecting a tool attachment to a tool driver of an electromechanical arm of a surgical robot, wherein the tool attachment includes an energy transducer and a memory, and wherein the tool attachment is in mechanical and electrical contact with the tool driver. The method also involves disconnecting the tool attachment from the tool driver, wherein the disconnecting removes a power supply to the tool attachment, and wherein calibration information related to the energy transducer is maintained in the memory after the power supply is removed. The method also involves connecting the tool attachment to a surgeon operated handle, wherein the surgeon operated handle reads the calibration information from the tool attachment.

In accordance with the method the memory includes at least information about a usage of the tool attachment. In addition, the energy transducer may comprise an ultrasonic energy transducer.

Some embodiments the tool attachment includes at least a battery to provide power to the tool attachment when the tool driver is disconnected from the tool attachment. The tool attachment also includes at least a wireless communication channel to communicate with the tool driver when the tool attachment is connected to the tool driver, to communicate with the tool driver when the tool attachment is not connected to the tool driver, and to communicate with the surgeon operated handle when the tool attachment is connected to the surgeon operated handle.

BRIEF DESCRIPTION OF THE DRAWINGS

The invention will be more fully understood from the following detailed description taken in conjunction with the accompanying drawings, in which:

FIG. 1 illustrates a perspective view of an embodiment of a surgical robotic system that includes a patient-side portion and a user-side portion with the patient-side portion including at least one robotic arm configured to releasably couple to a tool assembly;

FIG. 8A illustrates another embodiment of a puck of a tool assembly;

FIG. 8B illustrates an end-view of the puck of FIG. 8A;

FIGS. 11A and 11B illustrate an embodiment of a modular shaft that is swappable between a handle that can be manually manipulated (FIG. 11 A) and a robotic arm (FIG. 11B);

FIG. 12A illustrates another embodiment of a surgical tool including an adapter and a modular shaft configured in a robotic arm;

FIG. 12B illustrates an expanded view of the surgical tool of FIG. 12A with an adapter and a modular shaft;

FIG. 12C illustrates an expanded view of the surgical tool of FIG. 12A configured for use with a handle that can be manually manipulated;

DETAILED DESCRIPTION

Figure 2:
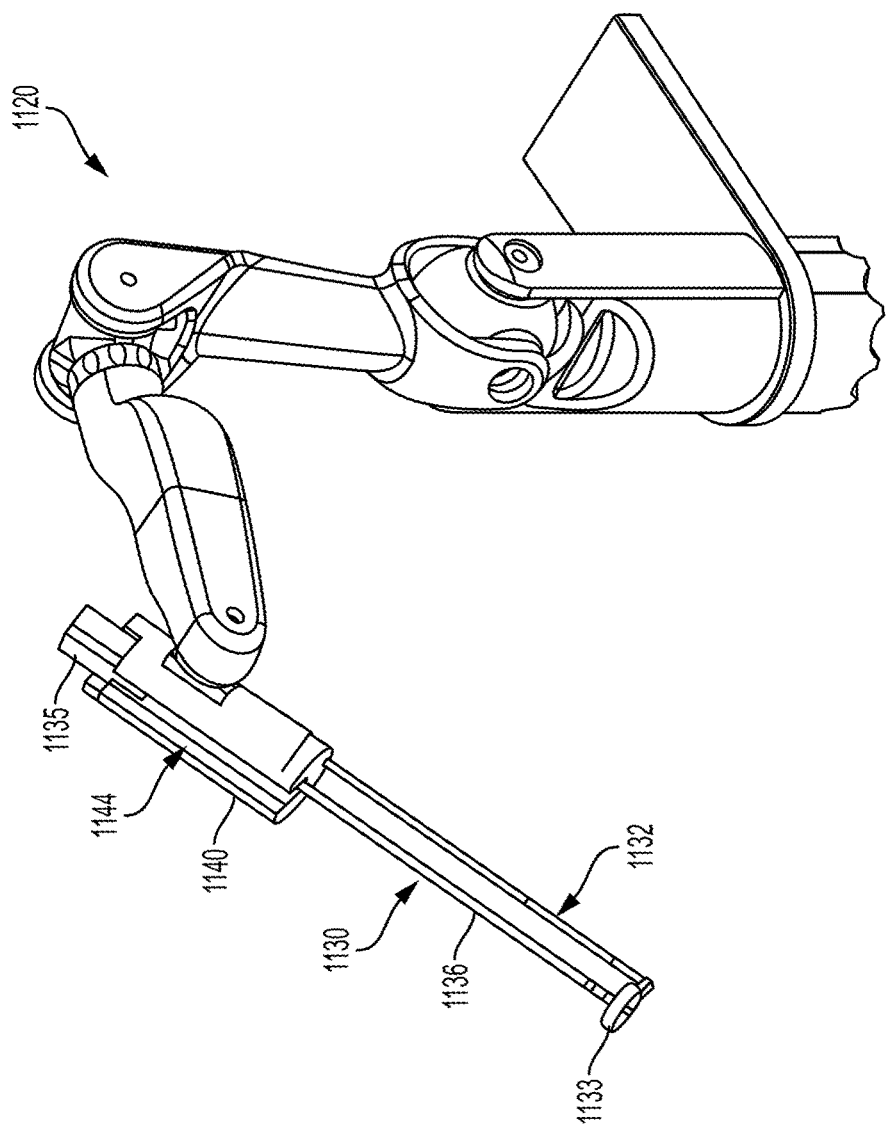
FIG. 2 illustrates an embodiment of the robotic arm of FIG. 1 having an embodiment of a tool assembly releasably coupled to the robotic arm.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The systems, devices, and methods disclosed herein can be implemented using a robotic surgical system.

In general, a surgical robotic system is described that can assist with performing surgical procedures on a patient. Such procedures can require the robotic surgical system to move at least one surgical arm and manipulate a tool assembly that is removably and replaceably coupled to each robotic arm. For example, a tool assembly can have an end effector that includes a cutting tool configured to assist with cutting tissue of a patient. The robotic surgical system can further include a control system that controls movement and manipulation of either the robotic arm or the tool assembly. In preparation for a surgical procedure, for example, a tool assembly can be releasably coupled to a first robotic arm and can be configured by the control system while coupled to the first robotic arm. The tool assembly can assist with performing one or more parts of a surgical procedure and subsequently uncoupled from the first robotic arm. After becoming uncoupled from the first robotic arm, the tool assembly can be either releasably coupled to a second robotic arm or used manually by a user. Such displacement of the tool assembly relative to the first robotic arm can result in loss of information related to the tool assembly, such as configuration information, location information, and status information. Such loss of information can be a result of the uncoupling of the tool assembly from the first robotic arm and can prolong surgical procedures due to the surgical robotic system having to either be re-calibrated or the user having to re-configure the tool assembly. As such, in order to provide continuous transfer of data and information between the tool assembly and the control system, the surgical robotic system described herein includes an embodiment of a wireless communication system that allows at least the tool assembly and control system to communicate wirelessly. This allows the control system to continue sending and receiving information to and from the tool assembly regardless of whether the tool assembly is coupled to the robotic arm thereby allowing seamless transfer of the tool assembly between robotic arms and/or manual use. As described in greater detail below, electronic communication between various components of the robotic surgical system can be either wired or wireless for assisting with seamless and continuing communication of data and information between at least the tool assembly and the control system.

In some embodiments, the tool assembly is modular and includes more than one modular part that can be either removed or interchanged. Such modularity can allow for easy replacement of one or more modular parts of the tool assembly, as well as allow for various configurations of the tool assembly. For example, a modular tool assembly can include an end effector that can be either removed or replaced, such as for switching tooling associated with the end effectors to assist with different parts of a surgical procedure. While removing, replacing, adding, and/or interchanging modular parts of one or more tool assemblies can provide advantages, such as allowing for a variety of tool assembly configurations, calibrating the modular tool assembly each time a modular part is removed, replaced, added, and/or interchanged can be time consuming. As such, in order to reduce procedure time and improve efficiency, the surgical robotic system described herein includes another embodiment of a wireless communication system that allows a modular part of a tool assembly to communicate with the control system, robotic arm, and/or other modular parts of the tool assembly (or another tool assembly). This allows configuration information to be communicated between the control system, robotic arm, and/or modular parts of tool assemblies thereby reducing or eliminating time required to re-configure a tool assembly after removing, replacing, adding, and/or interchanging one or more modular parts In some embodiments, a robotic surgical arm can include a tool assembly containing motors to drive an end effector. The tool assembly can generate ultrasonic and/or radio frequency energy to apply to tissue disposed between the jaws of the end effector. The tool assembly can include modular components such as a modular shaft that can include an ultrasonic transducer, nonvolatile memory, wireless interface, and/or a power source. The non-volatile memory can allow the modular shaft to be attached to one robotic arm and moved to another robotic arm without restarting or recalibrating the ultrasonic driver. The power source can allow the modular shaft to communicate wirelessly with the robotic arm while attached to a robotic arm, and after the modular shaft is detached from the robotic arm. The modular shaft can also be moved from a robotic arm to a handle manually controlled by a surgeon and back again to the robotic arm.

In some embodiments, a tool assembly can be "hot-swapped" or moved from one robotic arm to another while remaining powered. The tool assembly can include sensors to determine a location or movement of the tool assembly. A power source can allow the tool assembly to communicate wirelessly with the robotic while attached to a robotic arm and after the tool assembly is detached from the robotic arm. The tool assembly can also be moved from a robotic arm to a handle manually controlled by a surgeon and back again to the robotic arm.

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion. 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 can be included. Furthermore, the patient-side portion 310 can include separate robotic arms 320 mounted in various positions, such as relative to the surgical table 314. Alternatively, the patient-side portion 310 can include a single assembly that includes one or more robotic arms 320 extending therefrom.

FIG. 2 illustrates another embodiment of a robotic arm 1120 and a tool assembly 1130 releasably coupled to the robotic arm 1120. The robotic arm 1120 can support and move the associated tool assembly 1130 along one or more mechanical degrees of freedom (e.g., all six Cartesian degrees of freedom, five or fewer Cartesian degrees of freedom, etc.).

The robotic arm 1120 can include a tool driver 1140 at a distal end of the robotic arm 1120, which can assist with controlling features associated with the tool assembly 1130. The robotic arm 1120 can also include a movable tool guide 1132 that can retract and extend relative to the driver 1140. A shaft of the tool assembly 1130 can extend parallel to a threaded shaft of the movable tool guide 1132 and can extend through a distal end feature 1133 (e.g., a ring) of the movable tool guide 1130 and into a patient.

In order to provide a sterile operation area while using the surgical system, a barrier (not shown) can be placed between the actuating portion of the surgical system (e.g., the robotic arm 1120) and the surgical instruments (e.g., the tool assembly 1130) in the sterile surgical field. A sterile component, such as an instrument sterile adapter (ISA), can also be placed at the connecting interface between the tool assembly 1130 and the robotic arm 1120. The placement of an ISA between the tool assembly 1130 and the robotic arm 1120 can ensure a sterile coupling point for the tool assembly 1130 and the robotic arm 1120. This permits removal of tool assemblies 1130 from the robotic arm 1120 to exchange with other tool assemblies 1130 during the course of a surgery without compromising the sterile surgical field.

Figure 3:
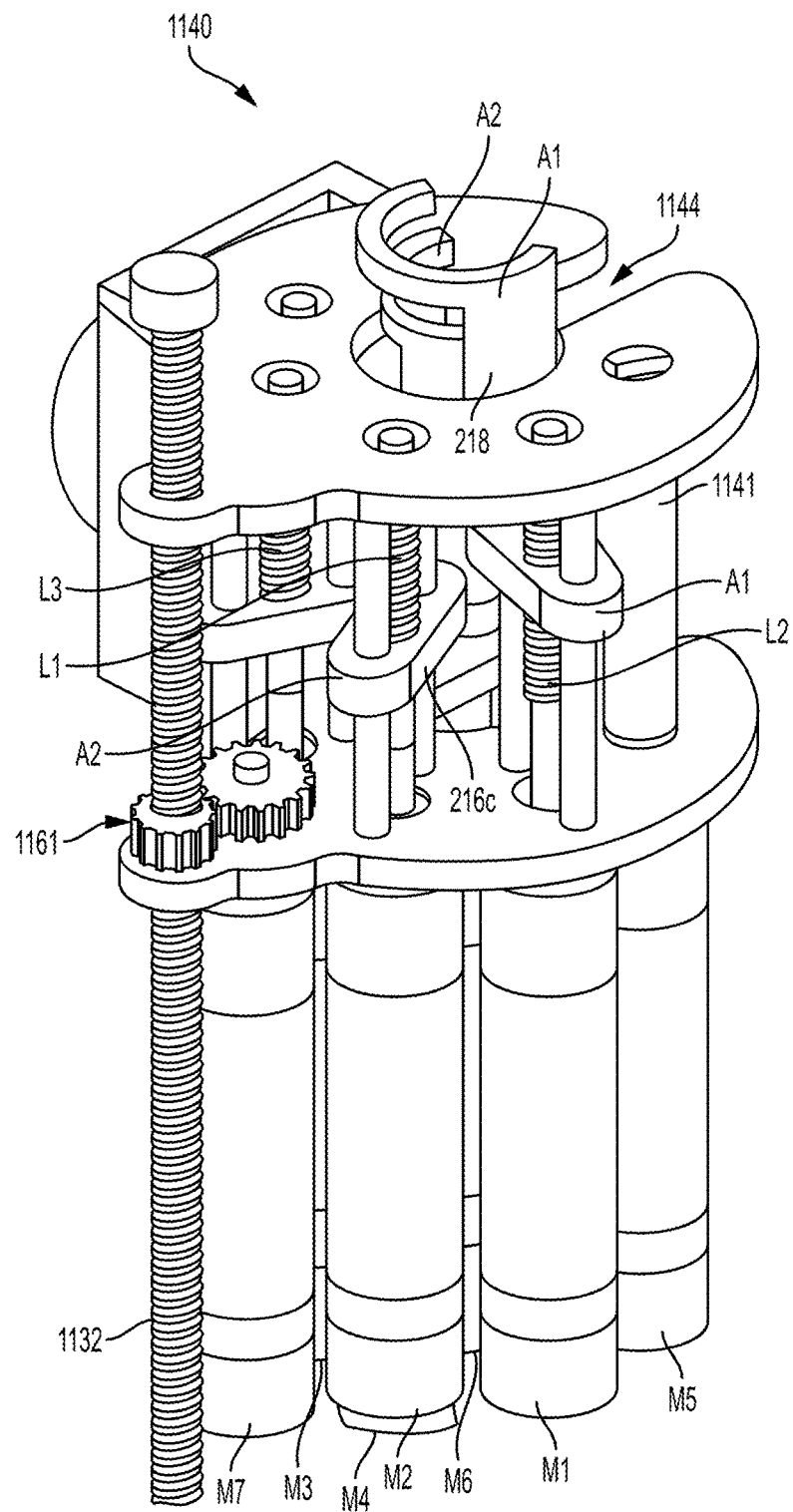
FIG. 3 illustrates a tool driver of the robotic arm of FIG. 2 having one or more motors that control a variety of movements and actions associated with the tool assembly.

FIG. 3 illustrates the tool driver 1140 in more detail. As shown, the tool driver 1140 includes one or more motors, e.g., seven motors M1-M7 are shown, that control a variety of movements and actions associated with the tool assembly 1130, as will be described in greater detail below. The driver 1140 can also include one or more lead screws (e.g., three lead screws L1, L2, and L3 are shown) that can be individually rotated by a motor and, as a result of the rotation of the lead screw, cause linear and/or rotational movement of at least one actuator (e.g., see, for example, actuators A1 and A2 shown in FIG. 3). Movement of each actuator controls the movement of driving members (e.g., gears, cables) located in the tool assembly 1130 for controlling one or more actions and movements that can be performed by the tooling assembly 1130, such as for assisting with performing a surgical operation. The actuators extend from a top end of the driver 1140 for coupling to the driving members of the tool assembly 1130 mounted on top of the tool driver 1140.

The tool assembly 1130 can be loaded from a top side of the driver 1140 with the shaft of the tool assembly 1130 being positioned in a shaft-receiving channel 1144 formed along the side of the driver 1140. The shaft-receiving channel 1144 allows the shaft, which extends along a central axis of the tool assembly 1130, to extend along a central axis of the driver 1140 when the tool assembly 1130 is coupled to the driver 1140. In other embodiments, the shaft can extend through on opening in the tool driver 1140, or the two components can mate in various other configurations.

Figure 4:
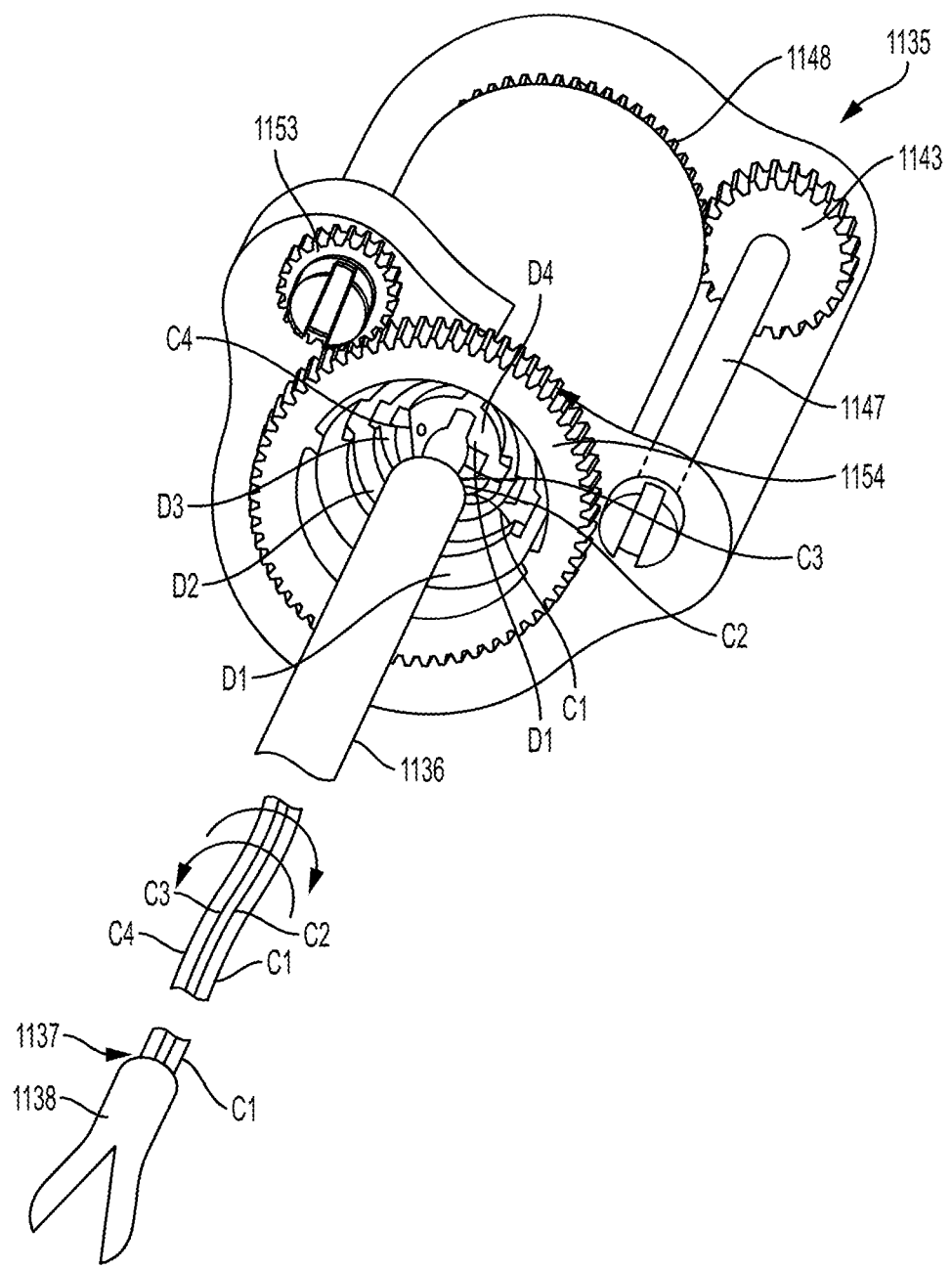
FIG. 4 illustrates a part of a puck actuation assembly contained within the puck of the tool assembly of FIG.
Figure 5:
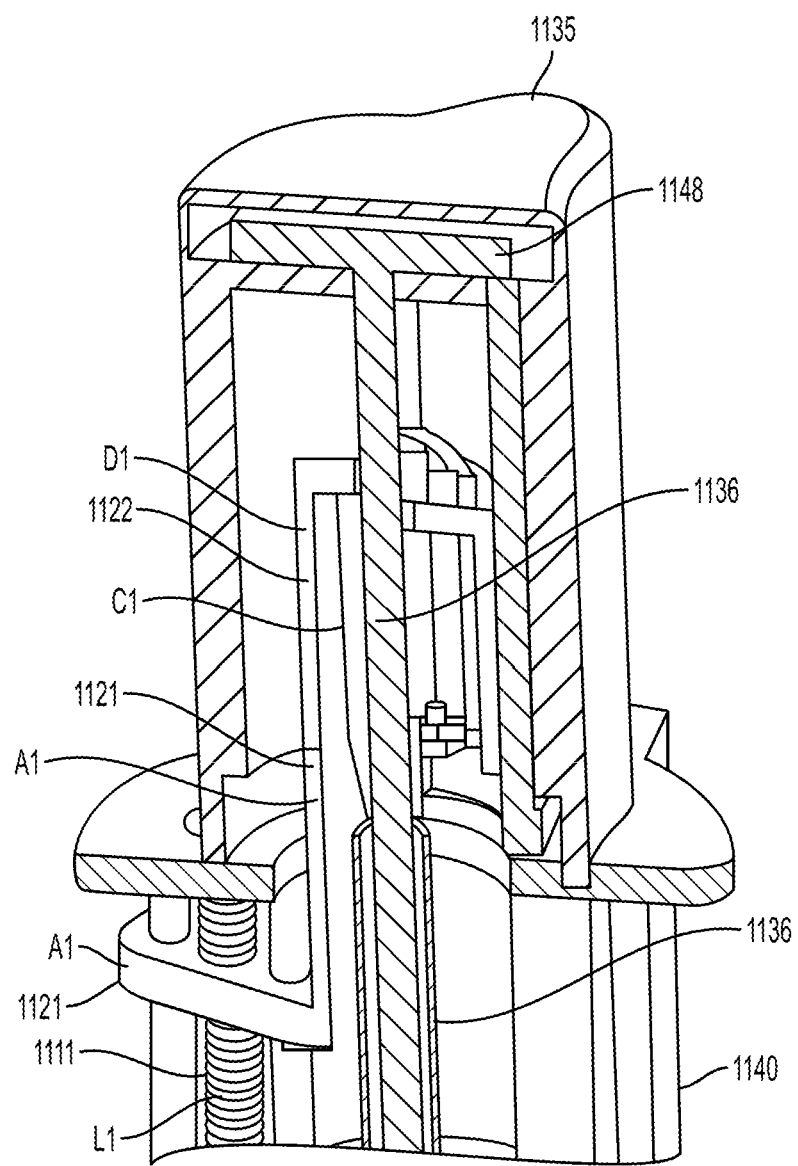
FIG. 5 illustrates the puck of FIG. 4 coupled to the driver with the actuators extending from the driver into the puck and engaging driving members.

As shown in FIGS. 4 and 5, the tool assembly 1130 includes a housing or puck 1135 coupled to a proximal end of a shaft 1136 and an end effector 1138 coupled to a distal end of the shaft 1136. The puck 1135 can include coupling features that assist with releasably coupling the puck 1135 to the tool driver 1140 of the robotic arm 1120. The puck 1135 can include driving members (e.g., gears, cables, and/or drivers) that can be directly or indirectly actuated by the one or more motors M1-M5, as will be described in greater detail below. The driving members in the puck 1135 can control the operation of various features associated with the end effector 1138 (e.g., clamping, firing, rotation, articulation, etc.), as well as control the movement of the shaft 1136 (e.g., rotation and/or articulation of the shaft).

The shaft 1136 can be releasably coupled to the puck 1135 such that the shaft 1136 can be interchangeable with other shafts. This can allow a single puck 1135 to be adaptable to various shafts 1136 having different end effectors 1138. The shaft 1136 can include actuators and connectors that extend along the shaft and assist with controlling the actuation and/or movement of the end effector 1138 and/or shaft 1136. The shaft 1136 can also include one or more joints or wrists 1137 that allow a part of the shaft 1136 or the end effector 1138 to rotate and/or articulate relative to the longitudinal axis of the shaft 1136. This can allow for fine movements and various angulation of the end effector 1138 relative to the longitudinal axis of the shaft 1136. The end effector 1138 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

FIG. 4 illustrates a part of a puck actuation assembly contained within the puck 1135. As shown in FIG. 4, the puck 1135 includes at least one driving member (e.g., four driving members D1, D2, D3, and D4 are shown) that can each become engaged with an actuator of the driver 1140 such that actuation of an actuator causes actuation of a driving member thereby controlling the operation of various features associated with the shaft 1136 and/or end effector 1138. Each driving member D1-D4 can be coupled to a proximal end of a shaft or cable (e.g., four cables C1, C2, C3, and C4 are shown). Each cable can extend from a driving member and couple to a feature associated with either the shaft 1136 or the end effector 1138 thereby controlling a function of such feature.

FIG. 5 illustrates the puck 1135 coupled to the driver 1140 with the actuators extending from the driver 1140 into the puck 1135 and engaging the driving members. For example, as shown in FIG. 3, motor M1 can cause lead screw L1 to rotate thereby causing actuator A1 which is threadably coupled to lead screw L1, to linearly advance in the proximal direction (towards and into the puck 1135). Actuator A1 can include an extension threadably coupled to the lead screw L1. The extension can be coupled to or integrated with a partial cylindrical shaft that extends along the longitudinal axis of the puck 1135 and the driver 1140. The partial cylindrical shaft of the actuator A1 can engage with driving member D1 such that when the actuator A1 is linearly advanced, the driving member D1 is caused to linearly advance in the same direction. Driving member D1 can be coupled to cable C1 such that when driving member D1 is advanced in the proximal direction, cable C1 is pulled in the proximal direction. Cable C1 extends along the shaft of the tool assembly 1130 and is operatively coupled to a part of the end effector 1138 thereby controlling a function of the end effector 1138 (e.g., opening and closing of jaws, deployment of a staple, etc.) when the cable is C1 translated in either the proximal or distal direction.

In some implementations, for example, four motors (e.g., M1-M4) can each individually control movement of a respective lead screw (e.g., L1-L4) thereby individually linearly translating a respective actuator (e.g., A1-A4) coupled thereto. Although the actuators are described as being linearly translated, the actuators can be linearly translated and/or rotationally moved as a result of actuation of a respective motor. Additional motors (e.g., motors M5 and M6) can be included in the driver 1140 for actuating various other aspects of the tool assembly 1130. For example, motor M5 can cause a first driver shaft 1141 to rotate, which is operatively coupled to a first puck shaft 1147 having a first puck gear 1143 coupled to a distal end of the first puck shaft 1147. Rotation of the first driver shaft 1141 thereby causes the first puck shaft 1147 and first puck gear 1143 to rotate. The first puck gear 1143 is engaged with a first shaft rotation gear 1148 that is caused to rotate as a result of the first puck gear 1143 rotating. The first shaft rotation gear 1148 is operatively coupled to the shaft 1136 of the tool assembly 1130 and can thereby cause rotation of the shaft 1136 and/or end effector 1138. Motor M6 can cause a second driver shaft to rotate, which is operatively coupled to a second puck gear 1153. The second puck gear 1153 is engaged with a second shaft rotation gear 1154 that is caused to rotate as a result of the second puck gear 1153 rotating. The second shaft rotation gear 1154 is also operatively coupled to the shaft 1136 and, upon rotation, provides additional torque through the shaft 1136 and for various features associated with the end effector 1138. Actuation of motor M7 can cause shaft gears 1161 to rotate, thereby causing the threaded shaft of the movable tool guide 1132 to linearly translate.

As discussed above, the robotic surgical system can include a wireless communication system that allows one or more parts of the robotic surgical system to communicate wirelessly with another part of the robotic surgical system. For example, a tool assembly can include a first wireless feature that can communicate (e.g., send and/or receive information) wirelessly to a second wireless feature associated with the control system, such as the control system 315 of FIG. 1. The first and second wireless features can communicate regardless of whether the tool assembly is coupled to the robotic arm. As such, information related to the tool assembly, including the end effector, can be communicated to the control system before, during, and/or after the tool assembly is uncoupled and moved away from the robotic arm, such as for coupling to a different robotic arm or for manual use. The information related to the tool assembly can be used under such new circumstances thereby reducing or eliminating the need to re-configure the tool assembly, as well as for keeping track of the location of the tool assembly (e.g., using one or more sensors associated with the tool assembly), as will be described in greater detail below.

Figure 6:
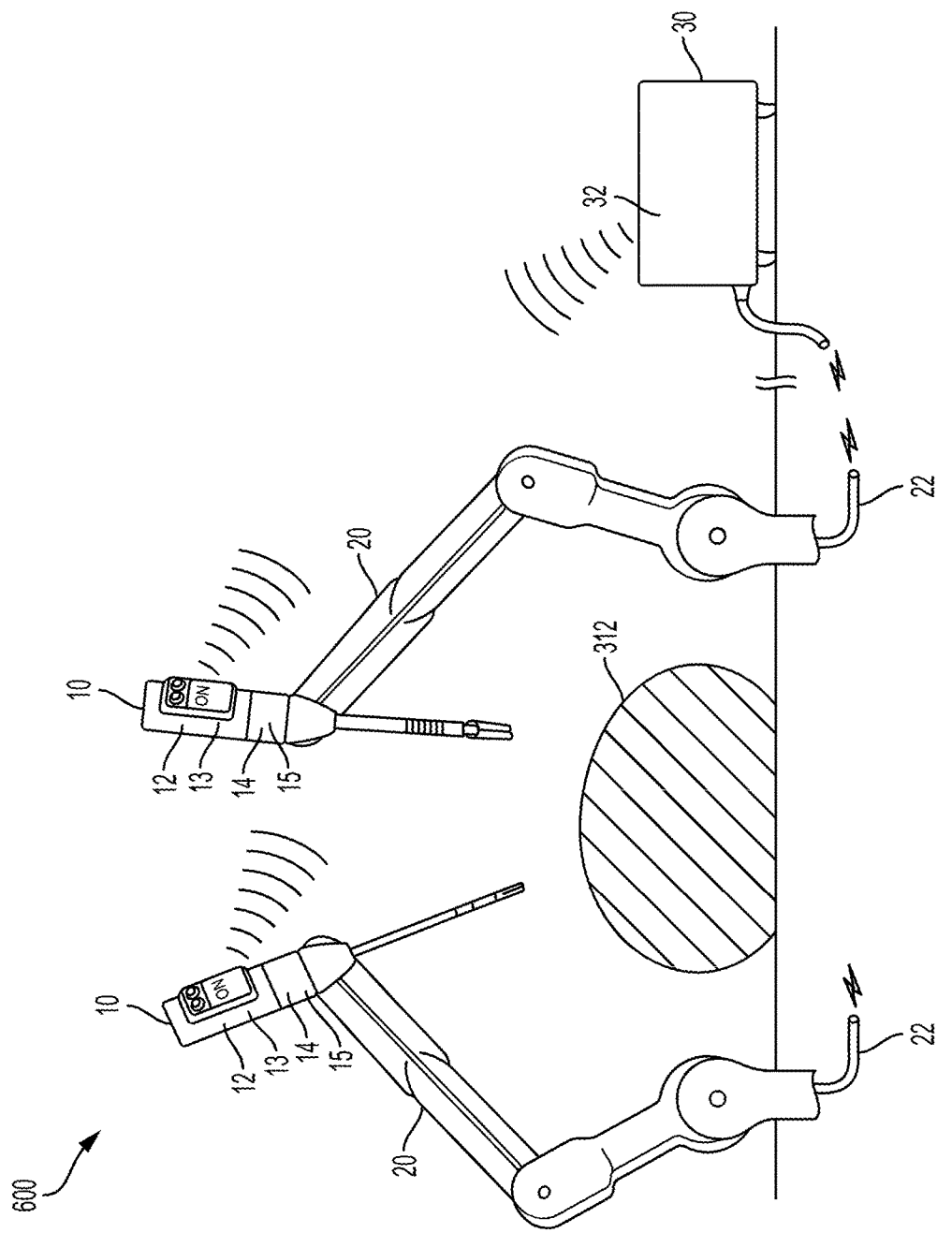
FIG. 6 illustrates another embodiment of a robotic surgical system that includes a wireless communication system.

FIG. 6 illustrates an embodiment of a robotic surgical system 600 similar to robotic surgical system 300 in FIG. 1. The robotic surgical system 600 can include a wireless interface 12 at tool assembly 10 to allow for communication between tool assembly 10 and wireless interface 32 at control system 30. The robotic surgical system 600 includes robotic arm 20 configured to releasably couple to tool assembly 10. In some embodiments, such as shown in FIG. 6, more than one robotic arm 20 and/or more than one tool assembly 10 may be included in robotic surgical system 600.

When robotic arm 20 is coupled to the tool assembly 10, the tool assembly 10 is both electrically and mechanically coupled to the robotic arm 20. In some embodiments, the tool assembly 10 is powered by the robotic arm 20 via electrical connectors associated with the tool assembly 10 and robotic arm 20, which are mated when the tool assembly 10 is coupled to robotic arm 20. The tool assembly 10 can be uncoupled from robotic arm 20 thereby mechanically and electrically disconnecting the tool assembly 10 from the robotic arm. Such electrical disconnection includes disconnecting the electrical connectors supplying power (and possibly control and status information) from the robotic arm 20 to the tool assembly 10. Upon disconnection of the electrical connectors, the tool assembly 10 can be powered by a battery 13, as described below. While powered by battery 13, tool assembly 10 does not shut down and can be used manually, such as by a surgeon after being coupled to a handle (not shown). Tool assembly 10 can also be re-coupled to either the same robotic arm 20 or coupled to a different robotic arm 20.

In some embodiments, the wireless tool interface of the tool assembly 10 includes a transducer, such as an ultrasonic transducer that produces ultrasonic energy, or a radio frequency generator that produces radio frequency energy. Such energy can be applied to a patient 312 by the tool assembly 10 for assisting with a surgical procedure (e.g., cutting tissue). Tool assembly 10 can include a generator that generates signals to drive the ultrasonic transducer and/or a generator that generates radio frequency energy. Calibration data may be needed to drive the ultrasonic transducer with one or more predefined amplitudes and/or frequencies. See FIGS. 8 and 9 for further description of an ultrasonic generator, an ultrasonic transducer, and radio frequency end effector.

As shown in FIG. 6, the wireless interface 12 at tool assembly 10 is configured to communicate with wireless interface 32 at control system 30. Wireless interfaces 12 and/or 32 can comply with Bluetooth, Bluetooth low-energy, WiFi, Zigbee, or any other wireless standard, or any proprietary wireless interface. A person skilled in the art will appreciate that communication protocols in addition to the wireless communication techniques noted above can also be used. Examples include acoustic communication (such as ultrasonic communication), optical data links, and magnetic data transfer. Tool assembly 10 can send status information to control system 30. For example, the status information can include data about the usage of the tool assembly, such as a number of uses or a number of cuts made by an end effector that is included in the tool assembly, a quantity of time that the tool assembly has been used, and a lifetime or charge status of a battery included in tool assembly 10A. other status information can also include fault detection recording and tool position when a tool is removed from a robotic arm. In some embodiments, calibration information used by an energy generator to drive a transducer in tool assembly 10A is sent or received via the wireless interface. See also the description below of FIGS. 8-11 for additional description of the calibration information.

In some embodiments, the tool assembly 10 includes one or more sensors for determining either a position or movement of the tool assembly 10. For example, the tool assembly 10 can include one or more inertial sensors, such as an accelerometer (single or multi-axis), a gyroscope, and/or one or more relative position sensors such as a magnetic sensor (single, or multi-dimensional). Data from one or more of such sensors can be processed at tool assembly 10A or sent via the wireless interface to control system 30 for processing. Processing the sensor data can determine the position of the tool assembly. For example, processing the sensor data can determine that tool assembly 10A is located at a position that is at the end of robotic arm 20B. From a change in location, control system 30 determines that the tool assembly 10A has been moved to robotic arm 20B. Alternatively (or in addition), the sensor data can be used to determine that the tool assembly 10 has moved a predetermined distance in a predetermined direction. For example, processing the sensor data can determine that the tool assembly 10 has moved approximately 32.1 inches in a direction pointing from the end of the robotic arm 20. From the distance and direction, control system 30 can determine that the tool assembly 10 has been moved to robotic arm 20. In some example embodiments, when a tool assembly 10A is removed from one robotic arm 20, and attached to another robotic arm 20, the tool assembly 10 has been "handed-off" to the other robotic arm 20.

In some embodiments, the robotic arm 20 can include a transfer arm that is configured to provide a second attachment point to which tool assembly 10 can releasably couple. The tool assembly 10 can include one or more attachment points to the transfer arm. The transfer arm can latch on to the tool assembly while the robotic arm is still attached to the tool assembly 10. The robotic arm 20 can uncouple from the tool assembly 10 and the transfer arm can remain connected to the tool assembly 10. The same or a different robotic arm 20 can couple to the tool assembly 10 and the transfer arm can thereafter uncouple from the tool assembly 10.

In some embodiments, a first robotic arm can be coupled to the tool assembly at a first attachment point of the tool assembly and a second robotic arm can be coupled to a second attachment point of the tool assembly. The first robotic arm can then uncouple from the tool assembly thereby leaving the second robotic arm coupled to the tool assembly. Some embodiments can include interchangeable shafts in the transfer arm. Exemplary robotic surgical systems are described in U.S. Pat. No. 8,931,682, entitled "Robotically-Controlled Shaft based Rotary Drive Systems for Surgical Instruments" and U.S. Patent Application Publication No. 2014/005718, entitled Multi-Functional Powered Surgical Device with External Dissection Features," both of which are incorporated herein by reference in the entirety.

In some embodiments, tool assembly 10 can include a battery 13. The battery 13 can supply power to the tool assembly 10 after the tool assembly 10 has been removed from the robotic arm. The battery 13 can power a processor, memory, sensors, and/or the wireless interface included in the tool assembly 10. In some embodiments, the battery 13 can enable an endocutter to be operated when unattached from a robotic arm 20. For example, the tool assembly 10 may include location and/or movement sensors. When tool assembly 10 is detached from robotic arm 20 battery 13 powers the sensors 14, the wireless interface 13, and a processor and memory 15. As the tool assembly 10A is moved, data from the location/movement sensors 14 can be processed at tool assembly 10A to determine location or movement of the tool assembly and the location or movement is sent to control system 30, or the tool assembly 10A. Alternatively (or in addition), the location/movement sensor data or the processed data can be sent to control system 30 for control system 30 to process and determine location/movement of the tool assembly 10A. In some embodiments, an endocutter tool assembly can be operated by a surgeon while detached from the robotic arm. The endocutter tool assembly can be attached to the same or a different robotic arm.

Figure 7:
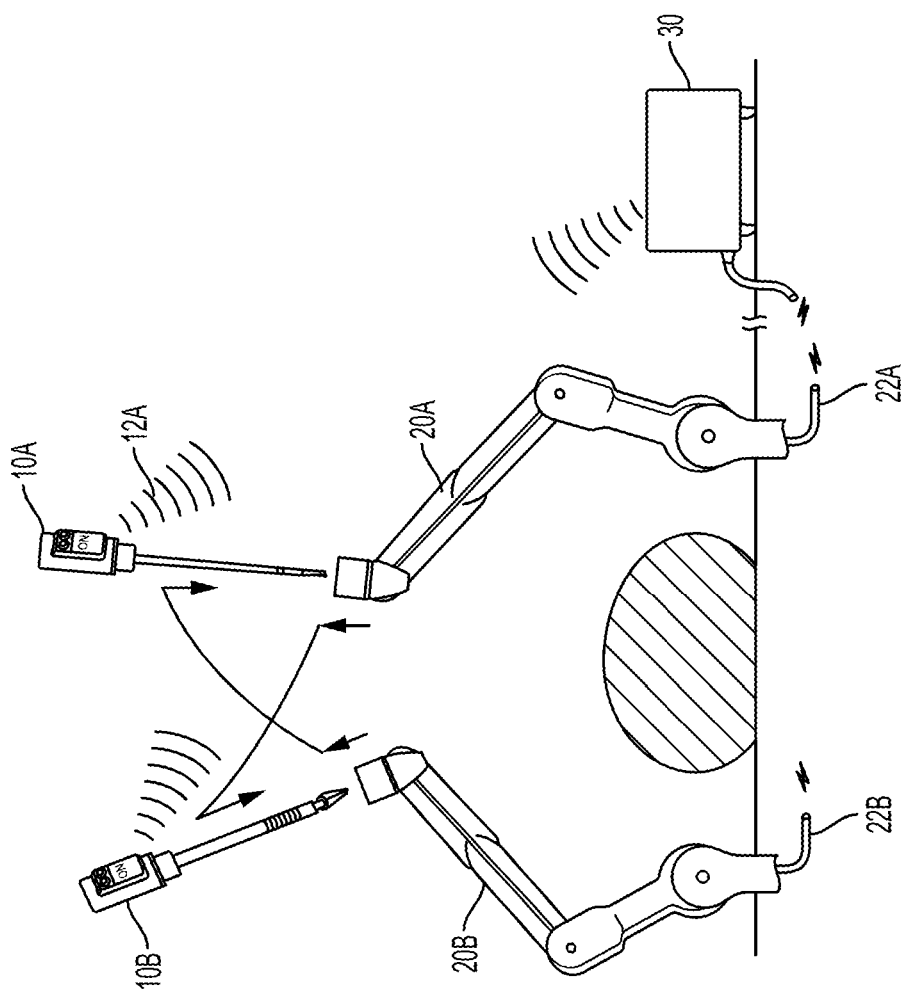
FIG. 7 illustrates transferring a tool assembly from a first robotic arm to a second robotic arm.

FIG. 7 illustrates tool assemblies 10A and 10B that can each include the features of tool assembly 10 in FIG. 6 including wireless interface 12, battery 13, sensors 14, and/or processor and memory 15. FIG. 7 illustrates decoupling a tool assembly 10A from a first robotic arm 20B and attaching the tool assembly 10A to a second robotic arm 20A, or the first robotic arm 20B at a later time. Before, during, and/or after the tool assembly 10A is removed from a first robotic arm 20B and attached to a second robotic arm 20A, the tool assembly 10A maintains a wireless connection to the control system 30. After removal from the first robotic arm 20B, the tool assembly 10A can be powered by the battery 13 included in the tool assembly 10 as described in FIG. 6 and FIGS. 8-12. As the tool assembly 10A is moved in position, the above-described location/movement sensors 14 can generate data that can be processed by processor and memory 15 at the tool assembly 10A or processed at control system 30 to periodically or intermittently determine the location of the tool assembly. A surgeon can operate tool assembly 10A while the tool assembly 10A is detached from robotic arms 20B and 20A. While detached, the tool assembly 10A can be powered by the battery 13 internal to tool assembly 10A or by a battery internal to a handle that can be releasably attached to tool assembly 10A as detailed with respect to FIGS. 10 and 11. Tool assembly 10A can maintain wireless communication with control system 30 while attached to a robotic arm 20B and while detached from a robotic arm 20B and used manually by a surgeon. Tool assembly 10A can be attached to a handle as described in FIGS. 10-12 for use by the surgeon.

As shown in FIG. 7, the tool assembly 10A can be attached to robotic arm 20B and tool assembly 10B can be attached to robotic arm 20A. Tool assembly 10A can be powered by connectors in tool assembly 10A and robotic arm 20B that are mated when the tool assembly is attached. Tool assembly 10B can be powered by connectors in tool assembly 10B and robotic arm 20A that are mated when the tool assembly is attached. In the example of FIG. 6, tool assembly 10A is removed from robotic arm 20B. After removal from robotic arm 20B, tool assembly 10A remains powered by the battery included in tool assembly 10A. As the tool assembly 10A is being removed and as the tool assembly 10A is moved, the above-described location/movement sensors can generate data that can be processed at the tool assembly or control system to periodically or intermittently determine the location of the tool assembly. The generated data and/or processed location/movement can be wirelessly transmitted to control system 30. Tool assembly 10A can be removed from robotic arm 20B and attached to robotic arm 20A. In a similar way, tool assembly 10B can removed from robotic arm 20A, data processed/transmitted, and 10B is attached to robotic arm 20B.

In some embodiments, a robotic surgical arm can include a modular attachment containing motors to drive an end effector. The modular attachment may include an ultrasonic generator to drive an ultrasonic transducer to produce ultrasonic energy to apply between the jaws of the end effector. The modular attachment may also include a radio frequency generator to produce radio frequency energy to apply between the jaws of the end effector. In some embodiments, the jaws of the end effector are or include electrodes that conduct the radio frequency energy to patient tissue disposed therebetween. The modular attachment can include modular components such as a modular shaft that can include the ultrasonic transducer, nonvolatile memory, and/or a power source. The non-volatile memory can allow the modular shaft to be attached to one robotic arm and then moved to another robotic arm without restarting or recalibrating the ultrasonic transducer. The power source can allow the modular shaft to communicate wirelessly with the robotic while attached to a robotic arm and after the modular shaft is detached from the robotic arm. The modular shaft can also be moved from a robotic arm to a handle manually controlled by a surgeon and back again to the robotic arm.

FIG. 8A illustrates an embodiment of a puck assembly 110 that can be included in a tool assembly, such as tool assembly 10A in FIG. 7 and/or tool assembly 10 in FIG. 6. FIG. 8B illustrates an end-view of puck assembly 110. Puck assembly 110 is a removable and replaceable module that can be coupled to a robotic arm 130. For example, a puck assembly 110 with ultrasonic transducer 122 can be removed and replaced with a puck with a radio frequency capability (not shown in FIG. 8A) and an ultrasonic transducer. Ultrasonic transducer 122 can be disposable. For example, ultrasonic transducer 122 can be used once, or used in one procedure, or on one patient, and then disposed and not used again. Puck assembly 110 can include a tool driver 120, circuit boards 114 and/or 116, battery 118, and motor 117 for shaft rotation, motor 119 for jaw clamping, and/or 121. Circuit boards 114 and/or 116 can produce electrical signals to drive an ultrasonic transducer, or to produce radio frequency energy that can assist in cauterizing blood vessels and tissue. Motors 117, 119, and/or 121 can control opening and closing of the end effector, rotation of the end effector, firing, articulation, etc. Puck assembly 110 can include a liquid crystal display (LCD) 112 to provide status and control information at a robotic arm.

Puck assembly 110 can include a wired or wireless interface to communicate with a robotic control system. For example a wireless interface can receive commands from a user side portion of a robotic system and/or send status information to the user side portion of the robotic system (see FIG. 1). Puck assembly 110 can include a processor and memory, motors, LCD display, ultrasonic and/or radio frequency energy generator, and a wireless interface to communicate with the user side portion. Wiring 102 from robotic arm 130 can carry power to puck assembly 110. In some embodiments, wiring 102 can also carry status and control information between puck 110 and a control system at the user side of the robotic system. In some embodiments, power is supplied through wiring 102 and status and control information is exchanged via a wireless interface. The wireless interface may comply with any standard such as Bluetooth, Bluetooth low-energy, WiFi, Zigbee, or any other standard, or any proprietary wireless interface, as discussed above.

Puck assembly 110 can include a non-volatile memory on one or more of circuit boards 114 and/or 116. The non-volatile memory can store status and configuration information for puck 110 that can include calibration data for an ultrasonic generator. For example, calibration information can be stored in non-volatile memory related to causing the particular ultrasonic transducer installed in tool driver 120 to produce one or more predefined ultrasonic frequencies at one or more predefined amplitudes. Ultrasonic transducers of the same type that are paired with a waveguide can behave differently to stimulus applied by an ultrasonic generator. These differences result in calibration information that is used to produce the predefined ultrasonic frequencies at the predefined amplitudes. Configuration information stored in memory can include usage information related to tool driver 120 and/or puck 110.

Puck 110 can include battery 118. In some embodiments, puck 110 can be moved from one arm of a robotic system to another arm of the robotic system without powering down puck 110. Battery 118 can provide power to circuit boards 114 and/or 116. In some embodiments, battery 118 can power circuit boards 116, 118 but can or can not power the motors, ultrasonic generator, or radio frequency generator. For example, when puck 110 is disconnected from power supplied by wire via 102, battery 118 can provide power to the processor, memory, and a wireless interface. Wireless communications can continue while the puck is being moved and until power is connected again by wire at the other robotic arm.

Figure 9:
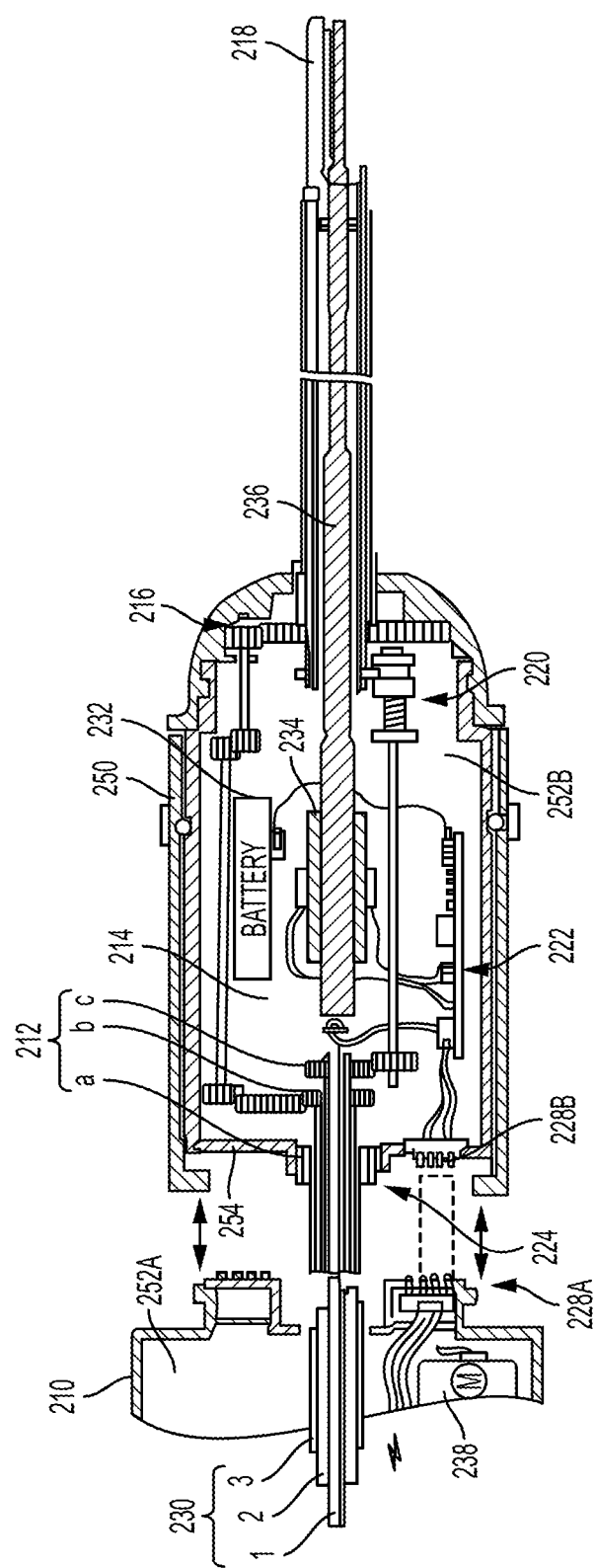
FIG. 9 illustrates an embodiment of a modular shaft of a tool assembly.

FIG. 9 illustrates a tool driver 210 releasably coupled to modular shaft 250. Tool driver 210 and modular shaft 250 may be included in puck assembly 110 of FIGS. 8A and 8B and/or tool assembly 10A of FIG. 7 and/or tool assembly 10 of FIG. 6. Modular shaft 250 can be attached to tool driver 210, and can be detached from tool driver 210. Modular shaft 250 can be detached from one tool driver 210 and attached to another tool driver 210. Tool driver 210 may include one or more motors 238 powering rotating drivers 230 (labeled 1, 2, and 3). Rotating drivers 230 can detachably interface with modular shaft 250. Tool driver 210 can include connector 228A that mates with connector 228B on modular shaft 250. When modular shaft 250 is attached to tool driver 210, rotating drivers 230 can cause rotation of spur gears 212 (labeled a, b, and c) inside modular shaft 250. Attaching modular shaft 250 to tool driver 210 causes an electrical connection to be made between connectors 228A and 228B that can supply power to modular shaft 250 and can and provide a wired interface for communication between the modular shaft 250 and tool driver 210.

Modular shaft 250 can include an ultrasonic transducer such as lateral ultrasonic transducer 214. Lateral ultrasonic transducer 214 can be coupled to waveguide 236 to guide ultrasonic energy to clamp jaw 218. Modular shaft 250 can include worm gear 220 to open and close clamp jaw 218. Modular shaft can also include spur gears 224 and/or 212. Modular shaft 250 can include processor 222 and can include memory and/or nonvolatile memory. The memory and/or nonvolatile memory can store configuration and/or calibration information. For example, the non-volatile memory can store calibration information related to the ultrasonic transducer 214, usage information related to ultrasonic transducer 214 (number of times used, total time used, manufacture date etc.), usage information related to modular shaft 250, clamp jaw 218, or tool driver 210, or battery charge status or battery lifetime information for battery 232. An ultrasonic generator 252B can be included in modular shaft 250 or can be included in tool driver 210 to generate stimulus to cause the ultrasonic transducer 214 to produce a predefined ultrasonic output. Modular shaft 250 can include battery 232 that can power one or more portions of modular shaft 250 when modular shaft 250 is disconnected from tool driver 210 as described above. Modular shaft 250 can include spur gear 216 to rotate an outer shaft and a clamp jaw 218. Modular shaft 250 can include worm gear assembly 220 to open and close clamp jaw 218. Modular shaft 250 can include spur gear assembly 224 to rotate inner housing 254.

Electrical power, control, and/or status information can flow through connectors 228A and 228B. In some embodiments, control and status information can be exchanged between modular shaft 250 and tool driver 210 via a wireless interface such as the wireless interfaces described above. In some embodiments, an ultrasonic generator 252A can be included in tool driver 210 and calibration and/or configuration information for the lateral ultrasonic transducer 214 can be stored in memory or non-volatile memory at modular shaft 250. When modular shaft 250 is removed from a tool driver, the ultrasonic generator 252A in tool driver 210 is detached from modular shaft 250. When modular shaft 250 is connected to another tool driver on another robotic arm, for example, the configuration and calibration information needed to drive lateral ultrasonic transducer 214 can be retrieved by the ultrasonic driver in the newly attached tool driver. The calibration and/or configuration information can be retrieved via the wireless interface described above or via electrical connection through connectors 228A and 228B.

Figure 10B:
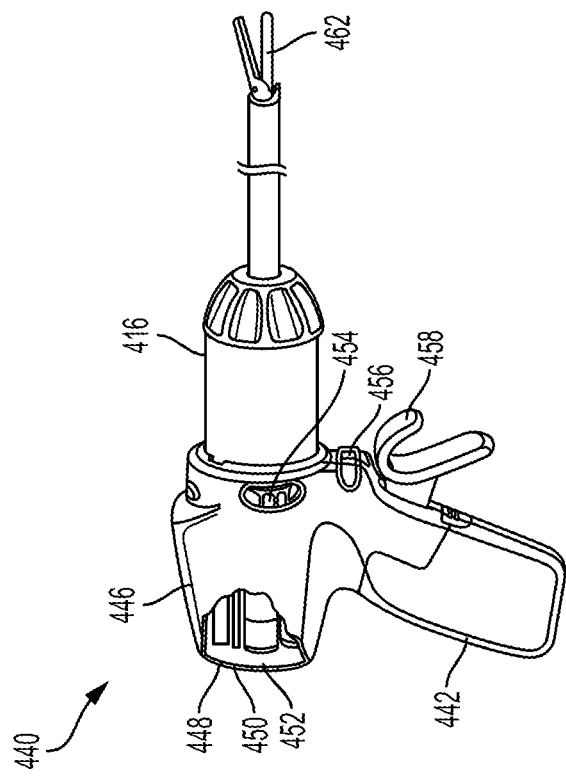
FIGS. 10A and 10B illustrate an embodiment of a modular shaft that is swappable from a robotic arm (FIG. 10A) and a handle that can be manually manipulated (FIG. 10B)
Figure 10A:
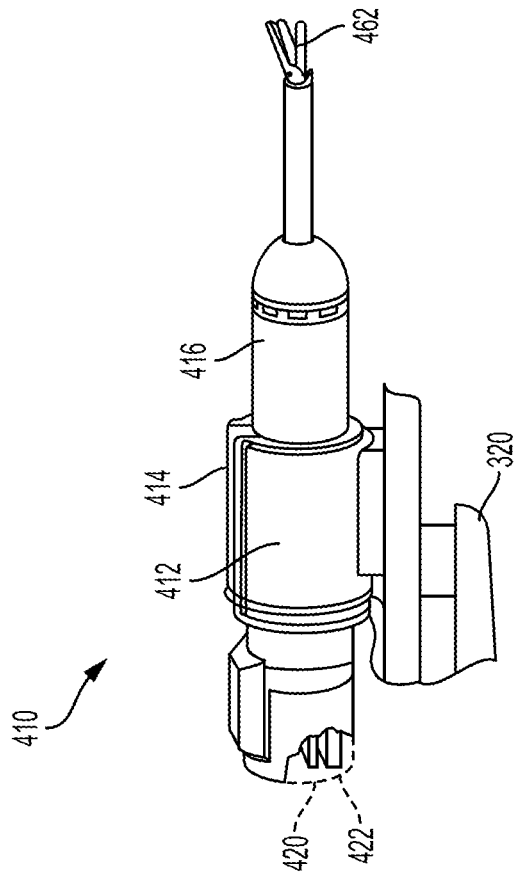

FIGS. 10A and 10B depict an example of a modular shaft that is swappable between a robotic arm at 410 (FIG. 10A) and a handle at 440 (FIG. 10B). Some aspects of modular shaft 416 are described with respect to FIGS. 8 and 9. At 410, modular shaft 416 is attached to tool driver 412, which is attached to robotic arm 320. An ultrasonic driver (also referred to herein as an ultrasonic generator) can be included in tool driver 412. A radio frequency generator can be included in tool driver 412, alternatively or in addition to the ultrasonic generator. Tool driver 412 can include one or more motors. Modular shaft 416 can include one or more of a non-volatile memory, processor, and/or battery. In some embodiments, the non-volatile memory can store calibration and configuration information as described above related to modular shaft 416.

Modular shaft 416 can be detached from tool driver 412 and attached to handle 442, as depicted at 440. Modular shaft 416 can also be detached from handle 442 and attached to tool driver 412, as depicted at 410. Handle 442 can include ultrasonic generator 448, radio frequency generator 450, motors 452, and/or LCD screen 446. Handle 442 can include a battery to power handle 442, or handle 442 can include a cable that supplies power. Handle 442 can include a wired or wireless status and control interface. Handle 442 can include controls 458 to open/close clamp jaw 462, a fire energy control 456 to cause ultrasonic/radio frequency energy to be applied/removed from clamp jaw 462, and/or shaft rotation control 454. In some embodiments, when modular shaft 416 is removed from robot tool 410 and attached to handle 442, the calibration and/or configuration information stored in the non-volatile memory in modular shaft 416 can be transferred to handle 442. The transfer of configuration and calibration information can allow the modular shaft 416 to be moved to the handle more quickly without requiring initialization and/or recalibration of the ultrasonic transducer paired with a new ultrasonic generator in the handle. The modular shaft can be similarly moved from the handle to the robotic arm.

FIGS. 11A and 11B depict another example of a modular tool that is swappable between a robotic arm and a handle. A hand operated tool at 500 in FIG. 11A includes tool driver 510, end effector 512, motors 520, and handle 530. Handle 530 can include a battery, a processor, an ultrasonic generator and/or a radio frequency generator. Tool driver 510 can include an ultrasonic transducer and/or radio frequency generator. Tool driver 510 can include a non-volatile memory that can store configuration and calibration data related to tool driver 510, the generator(s) in the tool driver, and/or end effector 512. Tool driver 510 and end effector 512 can be detached from handle 530 and attached to robotic arm 560 without requiring recalibration or restart of tool driver 510 as described above with respect to FIGS. 1-6. At 550 in FIG. 11B, moving the tool driver and end effector 512 from handle 530 to robotic arm 560, or moving the tool driver 510 and end effector 512 from robotic arm 560 to handle 530 can be performed without recalibration or restart of the tool driver 510. Moving the tool driver 510 without restart or recalibration can be referred to as "hot-swapping." A wireless interface included in tool driver 510 and handle 530 can allow calibration and configuration information to be shared between the tool driver 510 and handle 530. The wireless interface included in tool driver 510 and robotic arm 560 can allow calibration and configuration information to be shared between the tool driver 510 and robotic arm 560. Robotic arm 560 can include contacts 562 to supply power to tool driver 510. In some embodiments, tool driver 510, end effector 512, and handle 530 can be attached to robotic arm 560 without removal of the handle 530. In some embodiments, handle 440 in FIG. 10 can be handle 530.

FIG. 12A illustrates a surgical tool assembly 650 attached to robotic arm 640. The tool assembly 650 includes a tool driver 610, an adapter 620, and a modular shaft 625. In the illustrated embodiment, puck 615 is included as part of robotic arm 640. Puck 615 can include sterile barrier 617. Tool driver 610 can include separable pieces, including adapter 620 and modular shaft 625, and end effector 642.

FIG. 12B illustrates an expanded view of the tool assembly 650 shown in FIG. 12A. Modular shaft 625 can include an end effector 642, gears 643 for actuating/rotating the end effector, and a non-volatile memory 644. The non-volatile memory 644 can store information related to the status of the modular shaft 625 such as number of uses, times and dates of when the shaft was used, and/or location information relating to where the shaft was used. For example, location information can include one or more of: on which robotic arm the shaft was used, which surgical robot identified by a serial number, as well as the known physical location of the surgical robot. In some embodiments, the information stored in non-volatile memory can be transferred via wired electrical connections that are connected when modular shaft 625 is attached to adapter 620. The status information of modular shaft 625 can be transferred to tool driver 610 when adapter 620 (with modular shaft attached to the adapter) is attached to tool assembly 610. In some embodiment, modular shaft 625 and/or adapter 620 can include a wireless interface 645 and a battery 646 that can provide the status information to adapter 620 and/or tool driver 610 when modular shaft 625 is attached or detached from adapter 620.

FIG. 12C illustrates modular shaft 625 removed from the adapter 620 in FIGS. 12A and 12B, and attached to handle 630. Handle 630 can include a connector 647 to transfer status information from the non-volatile memory 644 in the modular shaft to the handle 630. In some embodiments, handle 630 can include a wireless interface 645 to receive status information from modular shaft 625 wirelessly.

Figure 13B:
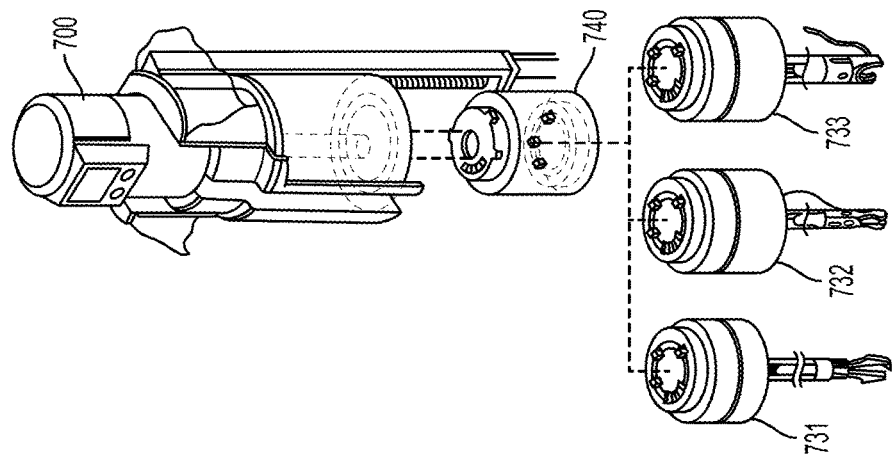
FIG. 13B illustrates various embodiments of modular tool drivers.
Figure 13A:
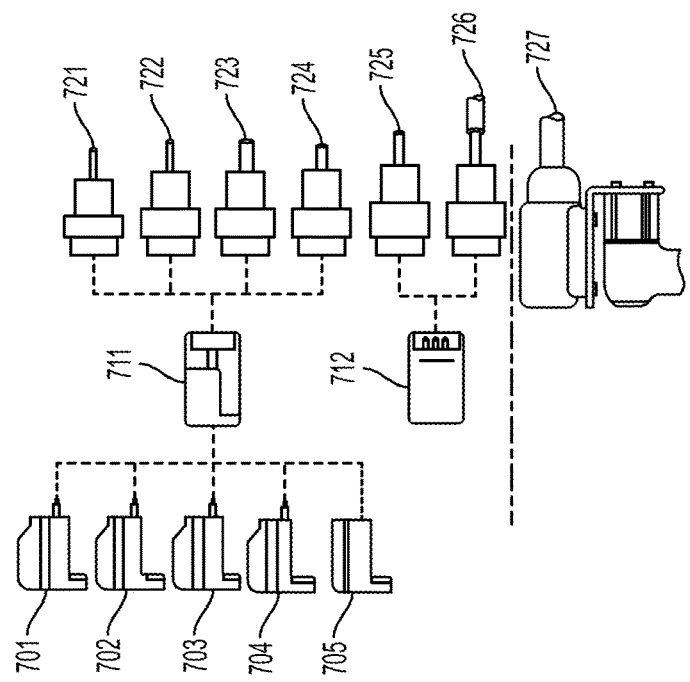
FIG. 13A illustrates various embodiments of modular transducers and modular shafts.

FIG. 13A depicts examples of modular transducers and modular shafts that can be attached to a tool assembly 700 and FIG. 13B depicts examples of modular tool drivers that can be attached to a tool assembly 700. Tool assembly 700 can include a transducer selected from a set of transducers, a tool driver selected from a set of tool drivers, and a shaft/nozzle selected from a set of shafts/nozzles. Examples of transducers include ultrasonic transducers 701, 702, combination transducer 703 including an ultrasonic transducer and a radio frequency end effector combination 704, and radio frequency end effector 705. Examples of tool drivers include ultrasonic and/or radio frequency tool driver 711 and stapling tool driver 712. Examples of shafts/nozzles include ultrasonic shaft 721, combination shaft 722 including ultrasonic shaft and radio frequency shaft, radio frequency shaft 723 with opposable jaw, radio frequency shaft 724 including an I-blade, linear stapler 725, shaft coupler 726, and circular stapler 727.

FIG. 13B depicts examples of modular tool drivers. A modular shaft adapter 740 can provide for the attachment to tool assembly 700 of hand-held tool drivers including clip applier 731 and stitching end effectors 732, 733.

Many benefits may be realized from the embodiments disclosed herein. For example, wireless communications between a tool driver (or tool assembly) and a control system reduces the number of wires required to interface between a robotic arm and tool driver which improves the reliability the wired interface and improves the reliability of communications between the tool driver and control system. Moreover, a tool driver with wireless communications and a battery for power allows for communications when the tool driver is detached from a robotic arm when being moved from one robotic arm to another or being used manually by a surgeon. Communications between modular components allows for configuration, usage, and calibration information to be exchanged between the modular components which provides for better automation of the operating room and improved data integrity over data recorded manually by surgical staff. Tool drivers with modular adapters improve the flexibility and number of uses a surgical robot may be used which in turn reduces the cost of robotic assisted surgeries.

Figure 14:
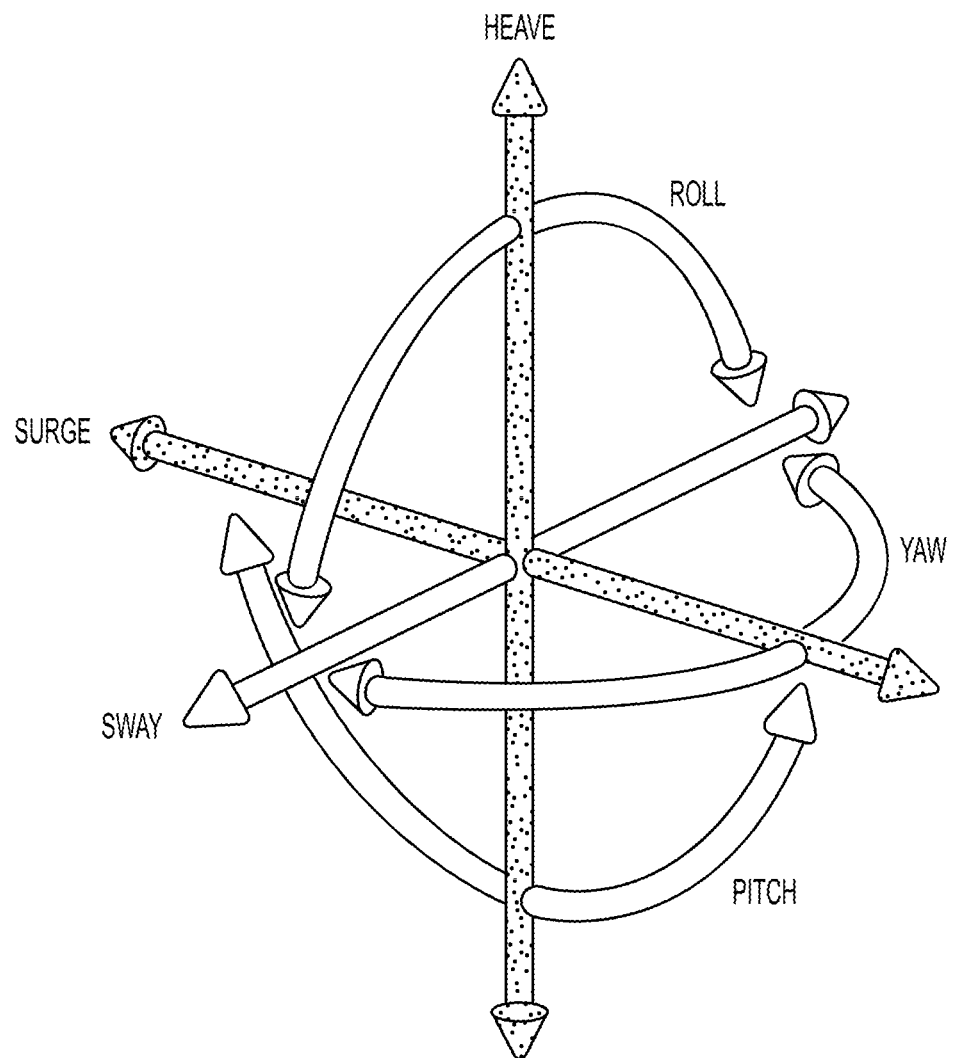
FIG. 14 illustrates movement and rotation along one of the three axes in a Cartesian frame.

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, and sway, and by the three rotational or orientation variables, e.g., Euler angles or roll, pitch, and yaw, that describe the position and orientation of a component of a surgical system with respect to a given reference Cartesian frame. As used herein, and as illustrated in FIG. 14, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientation variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes include various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 15:
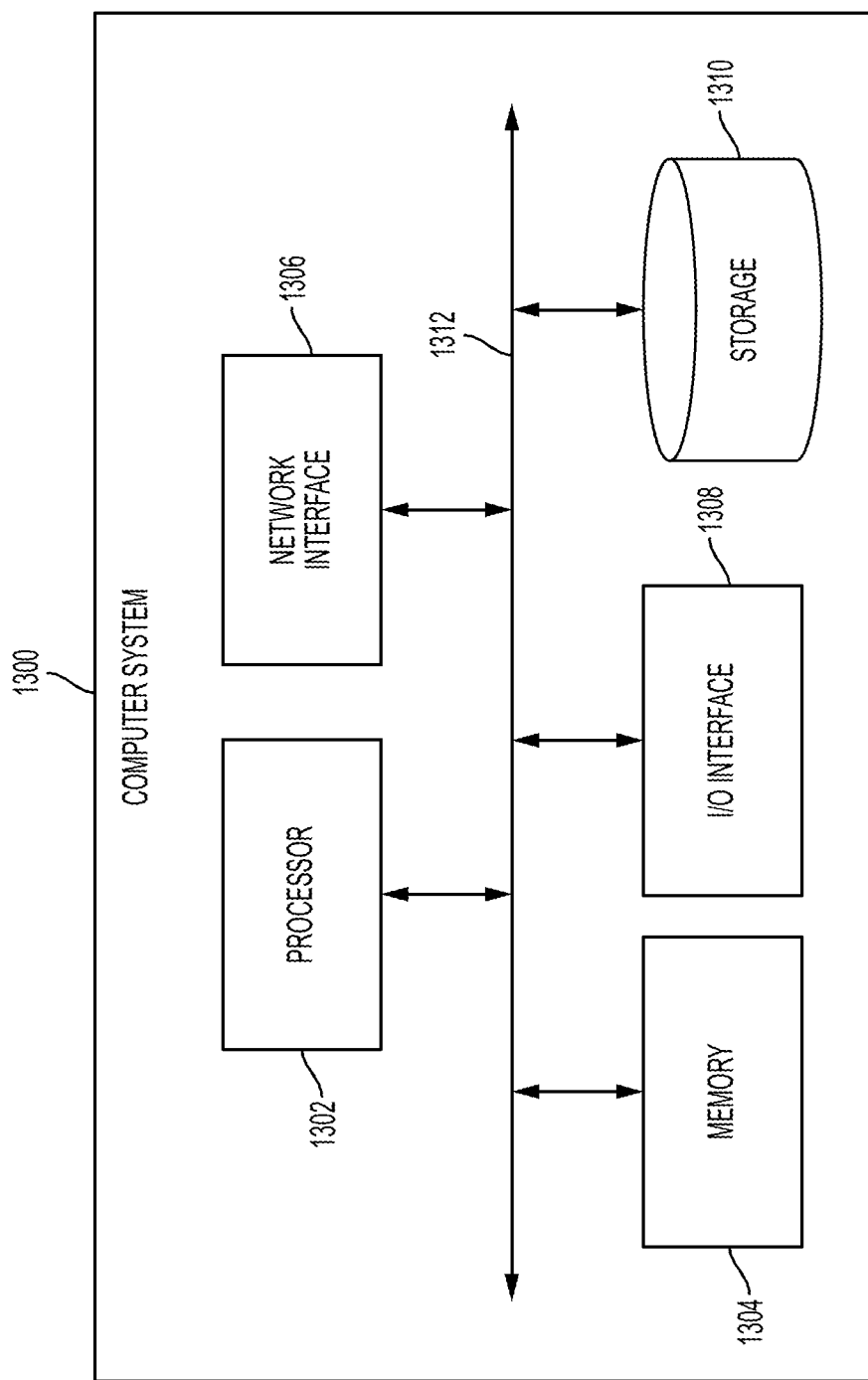
FIG. 15 illustrates an exemplary embodiment of a computer system.

FIG. 15 illustrates one exemplary embodiment of a computer system 1300. As shown, the computer system 1300 includes one or more processors 1302 which can control the operation of the computer system 1300. "Processors" are also referred to herein as "controllers." The processor(s) 1302 can include any type of microprocessor or central processing unit (CPU), including programmable general-purpose or special-purpose microprocessors and/or any one of a variety of proprietary or commercially available single or multi-processor systems. The computer system 1300 can also include one or more memories 1304, which can provide temporary storage for code to be executed by the processor(s) 1302 or for data acquired from one or more users, storage devices, and/or databases. The memory 1304 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 1300 can be coupled to a bus system 1312. The illustrated bus system 1312 is an abstraction that represents any one or more separate physical busses, communication lines/interfaces, and/or multi-drop or point-to-point connections, connected by appropriate bridges, adapters, and/or controllers. The computer system 1300 can also include one or more network interface(s) 1306, one or more input/output (IO) interface(s) 1308, and one or more storage device(s) 110.

The network interface(s) 1306 can enable the computer system 1300 to communicate with remote devices, e.g., other computer systems, over a network, and can be, for non-limiting example, remote desktop connection interfaces, Ethernet adapters, and/or other local area network (LAN) adapters. The IO interface(s) 1308 can include one or more interface components to connect the computer system 1300 with other electronic equipment. For non-limiting example, the IO interface(s) 1308 can include high speed data ports, such as universal serial bus (USB) ports, 1394 ports, Wi-Fi, Bluetooth, etc. Additionally, the computer system 1300 can be accessible to a human user, and thus the IO interface(s) 1308 can include displays, speakers, keyboards, pointing devices, and/or various other video, audio, or alphanumeric interfaces. The storage device(s) 1310 can include any conventional medium for storing data in a non-volatile and/or non-transient manner. The storage device(s) 1310 can thus hold data and/or instructions in a persistent state, i.e., the value(s) are retained despite interruption of power to the computer system 1300. The storage device(s) 1310 can include one or more hard disk drives, flash drives, USB drives, optical drives, various media cards, diskettes, compact discs, and/or any combination thereof and can be directly connected to the computer system 1300 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 15 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 1300 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 1300 can also include a web server for generating and/or delivering the web pages to client computer systems.

In an exemplary embodiment, the computer system 1300 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345, filed Feb. 8, 2008 and entitled "System And Method Of Sterilizing An Implantable Medical Device." It is preferred that a device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical tool, comprising:
   a tool attachment having a tool shaft extending distally therefrom with an end effector at a distal end of the tool shaft, wherein the tool attachment includes at least:
   a proximal end configured to mechanically and electrically connect to a tool driver, the tool driver supplying electrical power to the tool attachment when connected to the tool attachment;
   a position sensor configured to detect motion of the tool attachment relative to the tool driver when the tool attachment is operable and detached from the tool driver;
   a memory configured to store detected motion information and configuration information related to a usage of the tool attachment; and
   a wireless interface configured to transmit detected motion information and configuration information to a control system, wherein the control system is configured to determine a distance and a direction of motion of the tool attachment relative to the tool driver based on the detected motion information by the position sensor when the tool attachment is detached from the tool driver,
   wherein the wireless interface is configured to communicate with the tool driver when the tool attachment is connected to the tool driver, and to communicate with the tool driver when the tool attachment is not connected to the tool driver.

2. The surgical tool according to claim 1, wherein the tool attachment further includes a waveguide and the tool attachment is configured to be a disposable component.

3. The surgical tool according to claim 1, further comprising:
   a radio frequency generator, wherein the generator is configured to deliver radio frequency energy to at least one tissue contacting electrode disposed on the end effector.

4. The surgical tool according to claim 1, further comprising:
   a battery configured to provide power to the tool attachment when the tool driver is disconnected from the tool attachment.

5. The surgical tool according to claim 4, wherein the memory is configured to store information related to a calibration of an ultrasonic energy transducer in the tool attachment.

6. The surgical tool according to claim 1, wherein the tool attachment is removably and replaceably connected to the tool driver.

7. The surgical tool according to claim 1, wherein the tool attachment is configured to be releasably and replaceably connected to a surgeon operated handle.

8. The surgical tool according to claim 1, wherein the tool driver is attached to a robotic arm.

9. The surgical tool according to claim 8, wherein the tool attachment is connected to the tool driver at a first time, removed from the tool driver at a second time, and attached to a surgeon operated handle at a third time, wherein configuration and calibration information stored in the memory at the first time is read by a processor in the handle at the third time, wherein the third time is later than the second time and the second time is later than the first time.

10. The surgical tool according to claim 1, wherein the surgical tool is attached to a surgical robotic arm.

11. The surgical tool according to claim 1, wherein the tool attachment is removably and replaceably attached to a robotic arm, wherein the tool attachment is released from the robot arm, and wherein the tool attachment is attached to another robot arm.

12. A method, comprising:
   connecting a tool attachment to a tool driver of an electromechanical arm of a surgical robot, wherein the tool attachment includes an energy transducer, a position sensor configured to detect motion of the tool attachment relative to the tool driver; and a memory configured to store detected motion information and configuration information related to a usage of the tool attachment, and wherein the tool attachment is in mechanical and electrical contact with the tool driver;

disconnecting the tool attachment from the tool driver, wherein the disconnecting removes a power supply to the tool attachment, and wherein configuration information related to the energy transducer is maintained in the memory after the power supply is removed;

detecting, by a position sensor in the tool attachment, motion of the tool attachment relative to the tool driver when the tool attachment is disconnected from the tool driver;

connecting the tool attachment to a surgeon operated handle, wherein the surgeon operated handle reads the configuration information from the tool attachment; and transmitting, via a wireless interface, detected motion data to a control system, wherein the control system is configured to determine a distance and a direction of motion of the tool attachment relative to the tool driver based on the detected motion by the position sensor when the tool attachment is disconnected from the tool driver, wherein the tool attachment includes the wireless interface to communicate with the tool driver when the tool attachment is connected to the tool driver, to communicate with the tool driver when the tool attachment is not connected to the tool driver, and to communicate with the surgeon operated handle when the tool attachment is connected to the surgeon operated handle.

13. The method according to claim 12, wherein the energy transducer comprises an ultrasonic energy transducer.

14. The method according to claim 12, wherein the tool attachment includes at least a battery to provide power to the tool attachment when the tool driver is disconnected from the tool attachment.

* * * * *